(12) United States Patent
James et al.

(10) Patent No.: US 8,114,951 B2
(45) Date of Patent: Feb. 14, 2012

(54) PREPARATION AND USES OF POLYARYLATES

(75) Inventors: Ken James, Somerville, MA (US); Stephen Brochini, London (GB); Varawut Tangpasuthadol, Bangkok (TH); Joachim Kohn, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 12/533,953

(22) Filed: Jul. 31, 2009

(65) Prior Publication Data

US 2010/0063242 A1    Mar. 11, 2010

Related U.S. Application Data

(62) Division of application No. 10/889,914, filed on Jul. 13, 2004, now Pat. No. 7,585,929, which is a division of application No. 09/291,426, filed on Apr. 13, 1999, now abandoned.

(60) Provisional application No. 60/081,502, filed on Apr. 13, 1998.

(51) Int. Cl.
*C08G 63/06* (2006.01)

(52) U.S. Cl. ............. 528/182; 424/426; 506/20; 506/43
(58) Field of Classification Search .................. None
See application file for complete search history.

(56) References Cited

U.S. PATENT DOCUMENTS

| | | | | |
|---|---|---|---|---|
| 5,099,060 A | * | 3/1992 | Kohn et al. | .................. 560/40 |
| 5,587,507 A | * | 12/1996 | Kohn et al. | .................. 560/40 |
| RE37,160 E | * | 5/2001 | Kohn et al. | .................. 560/40 |
| RE37,795 E | * | 7/2002 | Kohn et al. | .................. 528/176 |

OTHER PUBLICATIONS

Brocchini et al (1997 JACS 119:4553-4554).*

* cited by examiner

*Primary Examiner* — Christopher M Gross
(74) *Attorney, Agent, or Firm* — Fox Rothschild LLP

(57) ABSTRACT

The present invention is directed to polyarylates comprising repeating units having the structure:

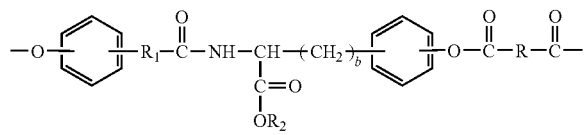

as well as their preparation and use as cell growth substrates.

9 Claims, 8 Drawing Sheets

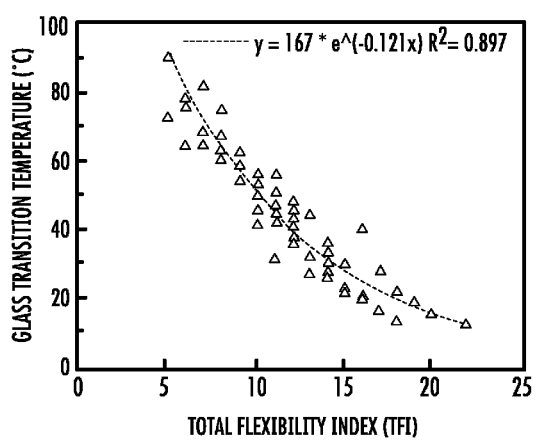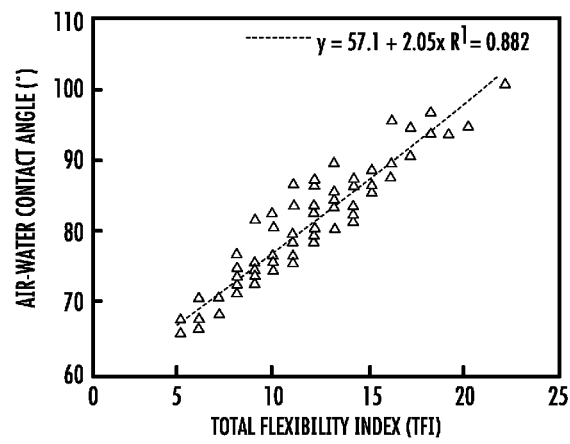
*FIG. 5A*  *FIG. 5B*

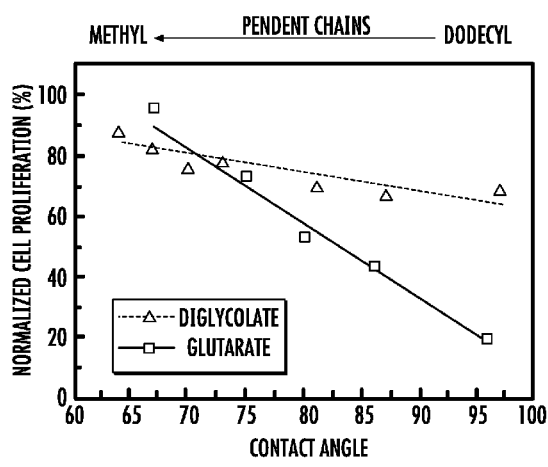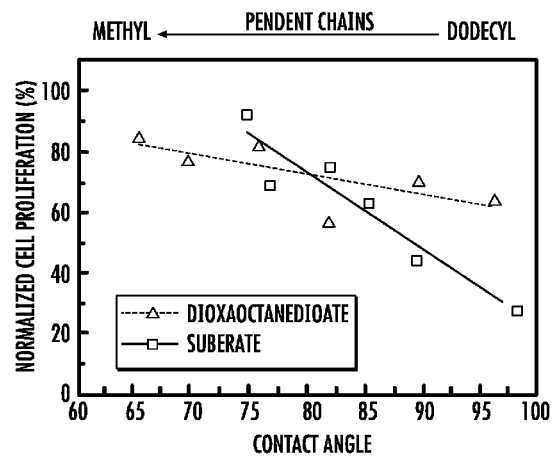
*FIG. 7A*  *FIG. 7B*

PREPARATION AND USES OF POLYARYLATES

CROSS-REFERENCE TO RELATED APPLICATION

This application is a divisional of U.S. patent application Ser. No. 10/889,914, filed Jul. 13, 2004, which is a divisional of U.S. patent application Ser. No. 09/291,426, filed Apr. 13, 1999, which claims priority benefit under 35 U.S.C. §119(e) to U.S. Patent Application Ser. No. 60/081,502, filed Apr. 13, 1998. The disclosures of all three applications are incorporated herein by reference.

GOVERNMENT LICENSE RIGHTS

The U.S. government has a paid-up license in this invention and the right in limited circumstances to require the patent owner to license others on reasonable terms as required by the terms of Grant No. GM-49849 awarded by the National Institutes of Health.

BACKGROUND OF THE INVENTION

The present invention relates to the construction of libraries of polymers based on the design principle of introducing systematic variations in the structure of a copolymer in at least two separate and independently variable domains within the copolymer structure. The inventive methodology is broadly applicable to the development of copolymers where complex requirements necessitate a careful optimization of copolymer structure.

This invention is also related to the preparation of tyrosine-derived monomers as disclosed in U.S. Pat. No. 5,587,507 and to the preparation and use of polyarylates as disclosed in U.S. Pat. Nos. 5,216,115 and 5,317,077, which are hereby incorporated by reference.

Combinatorial approaches that have led to dramatic changes in the way lead compounds for the discovery of new drugs are identified are disclosed by Lowe, *JCS Reviews*, 309-317 (1995). As usually practiced in the pharmaceutical industry, combinatorial schemes are used to create a large number of structurally related compounds (almost always within a single reaction vessel) followed by the identification of potential lead compounds in a selective bioassay. Such combinational schemes are disclosed by Mischer, *ChemTracts-Org. Chem.*, 8(1), 19-25 (1995). This approach is not readily applicable to the design of engineering polymers or biomaterials. Starting with a mixture of monomers and creating a large number of different polymers within the same reaction vessel would result in a blend of polymers that would be difficult to resolve into individual compounds. While such approaches are disclosed by EP 789,671 to be useful in the design of polymers with catalytic activities, these approaches are not useful for the design of polymers where individual material properties need to be optimized.

Correlations between chemical structure and the properties of polymers were explored since the early 1930's when the macromolecular structure of polymers was first recognized. Sometimes, materials are studied in "sets" of structurally unrelated materials. For example, studying the tensile strength of glass, iron, paper, wood, and polyethylene may lead to the identification of a material with suitable strength for any given application, however, because of the lack of any systematic variation in structure between the test materials, it is impossible to draw any generally useful conclusions from such a study.

A study design of somewhat greater sophistication is illustrated by Ertel et al., *J. Biomed. Mater. Res.*, 28, 919-930 (1994). A group of four polymers was investigated that had identical backbone structures but differed in the length of an alkyl ester pendent chain attached to the polymer backbone at each repeat unit. In this study, a relatively small number of polymers were compared and valid conclusions were drawn regarding the effect of increasing pendent chain length on selected polymer properties such as glass transition temperature, rate of chemical degradation etc. It is estimated that hundreds of studies of this kind have been reported in the literature. The main limitation of this study design is that only one single structural variable can be explored.

A study design of greater complexity attempts to correlate the effect of two or more structural variables on a set of selected materials properties. For example in the field of poly(acrylic acid) derivatives, a limited number of studies attempted to correlate the effect of simultaneous variations within the chemical structure of the acrylate pendent chains. Although such studies are known in the literature, the general paradigm of combinatorial synthesis has never been applied to the combinatorial synthesis of copolymers with systematic and defined structural features. In terms of the requirements for library design, this approach is unknown in the prior art.

Menger et al., *J. Org. Chem.*, 60, 6666-6667 (1995), exposed a preformed polymer with reactive pendent chains to a reaction mixture that contained a series of different reactants. As a random coupling procedure was initiated, random sequences of pendent chains were attached to the preexisting polymer backbone. In essence, this is an approach whereby an untraceable mixture of pendent chain sequences were all prepared at once. The individual sequences could not be isolated and no structurally defined materials were obtained. Rather, the entire mixture was tested for a specific catalytic activity and it was impossible to detect which particular pendent chain sequence was responsible for any observed catalytic activity.

Considering the cost and time required to identify carefully designed and optimized polymeric materials as "specialty polymers" in many different industrial, medical, and scientific applications, there is a great need to develop new paradigms and approaches that can (1) increase the number of candidate polymers available for any specific application and (2) systematize the study of correlations between polymer structure on one hand and material properties and performance on the other hand.

SUMMARY OF THE INVENTION

This need is met by the present invention. An important aspect of this invention is that systems of monomers is used in such a way that a large number of polymers can be synthesized in a parallel fashion so that each polymer contained within the resulting library is obtained in pure form in its own reaction vessel. One of the important advantages of this approach is that libraries of polymers are obtained which facilitate the establishment of simple and useful correlations between systematic changes in the chemical composition of the polymers on one hand and a wide range of physicomechanical and biological properties on the other hand.

The practical utility of this approach depends on a chemical design that provides for the formation of copolymers of the type A-B, or A-B-C, and so forth. In the example of A-B type copolymers, two sets of reactants $A_m$ and $B_n$, the copolymerization in all possible combinations of all monomers of set A with all monomers of set B will give a library with a total of A×B products. It has now been established that if the A and B monomers possess deliberate structural design features, the resultant library will be endowed with informative permutations of these characteristics.

The usefulness of this approach in rapidly developing large arrays of polymers with systematically varying properties can be further illustrated by the extension of this principle to polymers that are derived of more than 2 monomeric species. For example, using an A-B-C terpolymer design, the copolymerization of a set of 10 A's with 10 B's and 10 C's will give rise to 1000 different combinations. For sake of clarity, the following discussion is limited to strictly alternating A-B type copolymers with the understanding that the principles discussed can be readily extended to alternating polymers derived from more than two separate monomeric species.

Therefore, in accordance with the present invention, it is now possible to copolymerize a set of monomers derived from one structural template, with another set of monomers derived from a different structural template, so that the copolymerization of all members of the first set with all members of the second set in a preferably PARALLEL synthesis will lead to a library of copolymers in which the individual members of the library exhibit unusually systematic and regular variations in key end-use properties. Therefore, according to one aspect of the present invention, a multi-dimensional copolymer array is provided, comprising a plurality of copolymers polymerized from at least two independently variable sets of monomers, wherein the polymerization is characterized by:

(a) selecting a first homologously varying series of monomers with non-varying polymerizable functional groups;

(b) selecting at least one additional homologously varying series of different monomers having non-varying polymerizable functional groups that are reactive with the polymerizable functional groups of the first series of monomers to form copolymers; and (c) separately reacting a plurality of monomers from the first monomer series with a plurality of monomers from each of the additional monomer series to form the plurality of copolymers;

wherein the homologous variations of the monomer series are selected to determine the effect of independently varying at least two different structural features of the copolymer on at least one end-use property of the copolymer.

The copolymers include both condensation-type copolymers and copolymers prepared by free-radical polymerization. The homologous variations within each monomer series are preferably selected to minimize any effect upon the reactivity of the polymerizing functional groups of the monomers within each series.

For purposes of the present invention, homologous series are defined not only as relating to substituent groups on a series of monomers, but also including variations within the monomer backbone structure such as the introduction of unsaturation, the inclusion of additional methylene units, the replacement of a methylene carbon with a nitrogen or any other suitable atom, the replacement of a methylene unit with an oxygen or sulfur atom, or any other suitable atom, the replacement of a methylene unit with another unit including, but not limited to, a keto-unit, an amide unit, or an ester unit, and the like. For purposes of the present invention, hydrogen is treated as a member of homologous substituent series.

To obtain a library of polymers where selected end-use properties change in a predictable and systematic fashion, the monomer sets A and B must be designed to provide complementary structural variations. Preferred target end-use properties for investigation include glass transition temperature, surface tension, and biological interaction with living cells.

The unique utility of such polymer libraries is twofold. The approach as described here can be used to (1) increase the number of candidate polymers available to be evaluated for any specific application and (2) systematize the study of correlations between polymer structure, end-use properties, and performance.

Therefore, according to another aspect of the present invention, a method is provided for determining the effect of independently varying at least two different structural features of a copolymer on an end-use property of the copolymer, which method includes the steps of:

(a) measuring at least one end-use property of each of a plurality of copolymers prepared according to the present invention; and (b) comparing the variations in each end-use property measured for each of the copolymers as a function of the homologous variation within the monomer series from which the copolymers were polymerized to determine any relationship between the homologous variations and the end-use property variations among the copolymers;

thereby identifying specific members of the plurality of copolymers having useful properties for specific end-uses.

Through the use of the inventive methodology it was unexpectedly discovered that polyarylate copolymers, prepared by the condensation of a tyrosine-derived diphenol compound and a dicarboxylic acid, and having an ether linkage in either the polymer backbone or the polymer side chain were good cell growth substrates despite being very hydrophobic. Therefore, according to another aspect of the present invention, polyarylates are provided having repeating units with the structure of Formula I:

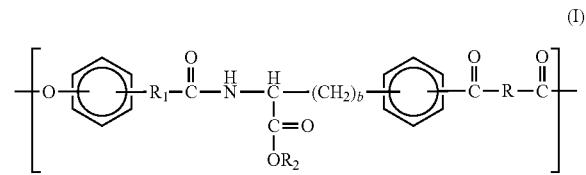

wherein R is selected from saturated and unsaturated, substituted and unsubstituted, alkyl and alkylaryl groups containing up to 18 carbon atoms;

$R_1$ is selected from —CH═CH—, $(-CH_2-)_a$ and —CHN($L_1L_2$)—, in which a has a value from zero to eight, inclusive, and $L_1$ and $L_2$ are independently selected from hydrogen and straight and branched alkyl and alkylaryl groups having up to 18 carbon atoms, provided that $L_1$ and $L_2$ are not both hydrogen;

b independently has a value from zero to eight, inclusive; and $R_2$ is selected from hydrogen and straight and branched alkyl and alkylaryl groups containing up to 18 carbon atoms;

wherein one or more of $R_1$ and $R_2$ and, when $R_1$ is —CHNL$_1$L$_2$, $L_1$ and $L_2$, contain at least one ether linkage.

The polyarylate copolymers of the present invention having ether linkage-containing side chains are the condensation product of a dicarboxylic acid with a tyrosine-derived diphenol compound having at least one side chain containing at least one ether linkage. These diphenol compounds are novel and non-obvious in view of their unexpected ability to condense with a dicarboxylic acid to form a polyarylate copolymer that is unexpectedly both a good cell growth substrate and very hydrophobic. Therefore, according to another aspect of the present invention, a tyrosine-derived diphenol compound is provided having the structure of Formula II:

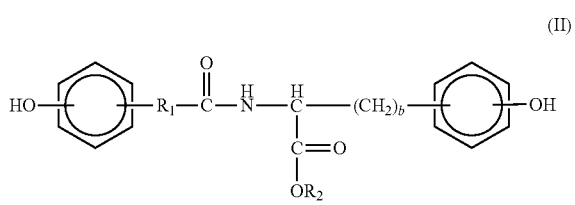

(II)

wherein $R_1$, $R_2$, and b are the same as described above with respect to Formula I, with the proviso that $R_2$, and/or, when $R_1$ is —$CHNL_1L_2$, at least one of $L_1$ and $L_2$, contains at least one ether linkage.

A more complete appreciation of the invention and many other intended advantages can be readily obtained by reference to the following detailed description of the preferred embodiment and claims in conjunction with the accompanying drawings, which disclose the principles of the invention and the best modes which are presently contemplated for carrying them out.

BRIEF DESCRIPTION OF THE DRAWINGS

FIG. 5a depicts the correlation between $T_g$ and the number of carbon atoms incorporated at the modification points of the polymer backbone and pendent chain, expressed as the total flexibility index (TFI);

FIG. 5b depicts the correlation between air-water contact angle and the number of carbon atoms incorporated at the modification points of the polymer backbone and pendent chain;

FIG. 7a depicts the correlation between fibroblast proliferation and surface hydrophobicity for poly(DT ester glutarates) and poly(DT ester glycolates); and FIG. 7b depicts the correlation between fibroblast proliferation and surface hydrophobicity for poly(DT ester suberates) and poly(DT ester dioxaoctanedioates).

DETAILED DESCRIPTION OF THE PREFERRED EMBODIMENT

The general concept of the present invention and its application to biomaterials development is illustrated here for polyarylate copolymers prepared by the condensation of a diacid with a diphenol according to the method described by the above-referenced U.S. Pat. No. 5,216,115, in which diphenol compounds are reacted with aliphatic or aromatic dicarboxylic acids in a carbodiimide mediated direct polyesterification using 4-(dimethyl-amino) pyridinium-p-toluene sulfonate (DPTS) as a catalyst. However, one of ordinary skill in the art will understand how this concept may be extended to other condensation or free radical polymerization reactions for other end-uses in addition to the preparation of biomaterials.

For example, in addition to monomer series in which the polymerizable functional groups are hydroxyl and carboxylic acid groups, other monomer series suitable for use with the present invention in condensation-type polymerization reactions include monomers having polymerizable amino, ester, anhydride, and isocyanate functional groups. The polymerizable functional group may also be activated to react with the polymerizable functional groups of the other monomer series.

When the polymerizable functional group of the first monomer series is a hydroxyl or amino group, monomer series suitable for use as additional monomer series include monomer series in which the polymerizable functional group is a carboxylic acid, isocyanate, ester or anhydride group. For condensation reactions in which two additional monomer series are employed, the second additional monomer series include alkylene oxide monomers. Examples of suitable alkylene oxide monomers include ethylene oxide, propylene oxide, isopropylene oxide, butylene oxide, isobutylene oxide and block and random copolymer segments thereof.

Condensation-type polymerization reactions include both interfacial and suspension processes. However, the present invention also includes copolymers prepared by free radical processes including ionic polymerization processes.

The synthesis reactions may be performed in solution or in bulk and with or without a catalyst. The reaction products may be further modified by chemical reactions or by crosslinking. Such synthesis features are well-known to those of ordinary skill in the art and require no further explanation.

A particularly preferred monomer series for use as the first monomer series are the tyrosine-derived diphenol monomers of U.S. Pat. Nos. 5,587,507 and 5,670,602, the disclosures of both of which are also incorporated herein by reference. The preferred diphenol monomers are desaminotyrosyl-tyrosine esters, which are referred to as DT esters. For purposes of the present invention, the ethyl ester is referred to as DTE, the benzyl ester as DTBn, and so forth. Both patents disclose methods by which these monomers may be prepared. As noted above, the diphenol monomers may be employed in the synthesis of the polyarylates disclosed by U.S. Pat. No. 5,216,115.

Figure 3:
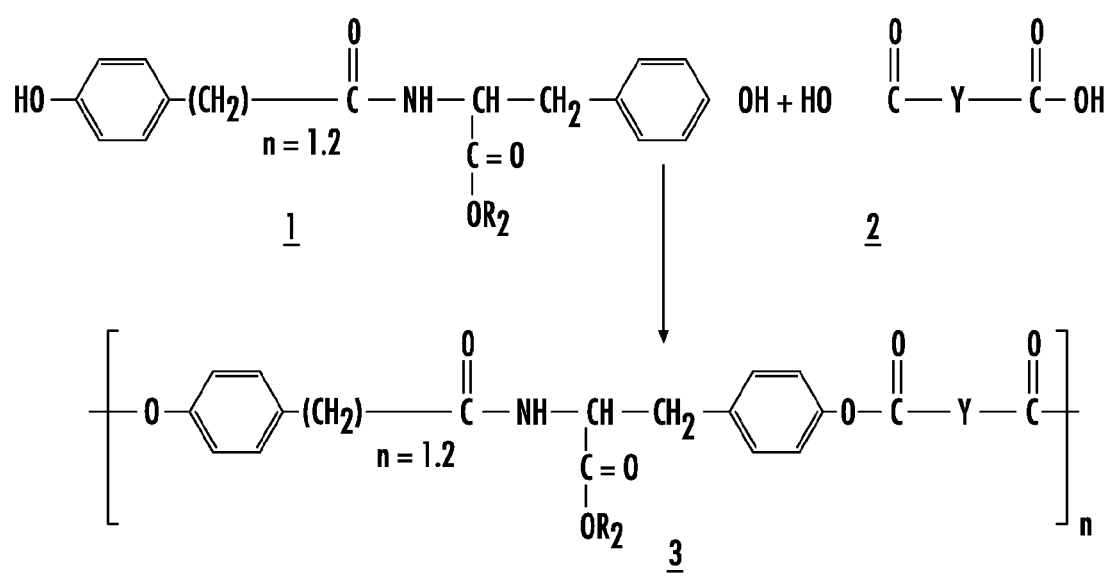
FIG. 3 depicts the general structure of polyarylates in accordance with the present invention.

The general structure of polyarylates is shown in FIG. 3. These materials are strictly alternating A-B type copolymers consisting of a diacid component (the "A" monomers) and a diphenol component (the "B" monomers). The diacids allow for variation in the polymer backbone while the diphenols contain a moiety for appending and varying a pendent chain. While the diphenol is a tyrosine-derived dimer, it functions as a single monomer unit in the condensation reactions of the present invention, so that the condensation product of the diphenol with the diacid is considered a strictly alternating polyarylate copolymer when a third homologous monomer series is not employed.

Figure 4A:
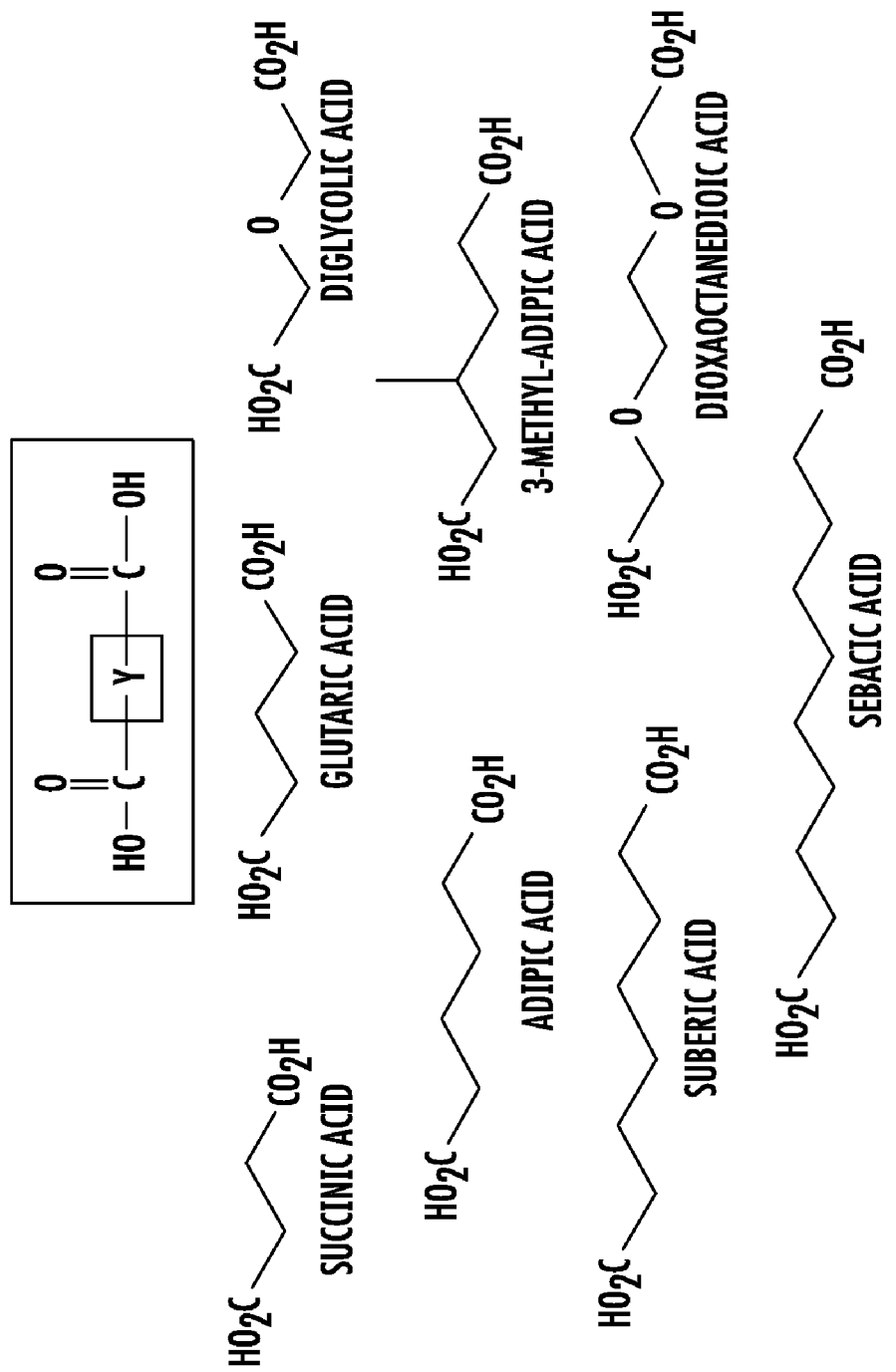
FIGS. 4a and 4b depict the first and second homologous series of monomers employed in the method of the present invention to create the polyarylate copolymers of the present invention.
Figure 4B:
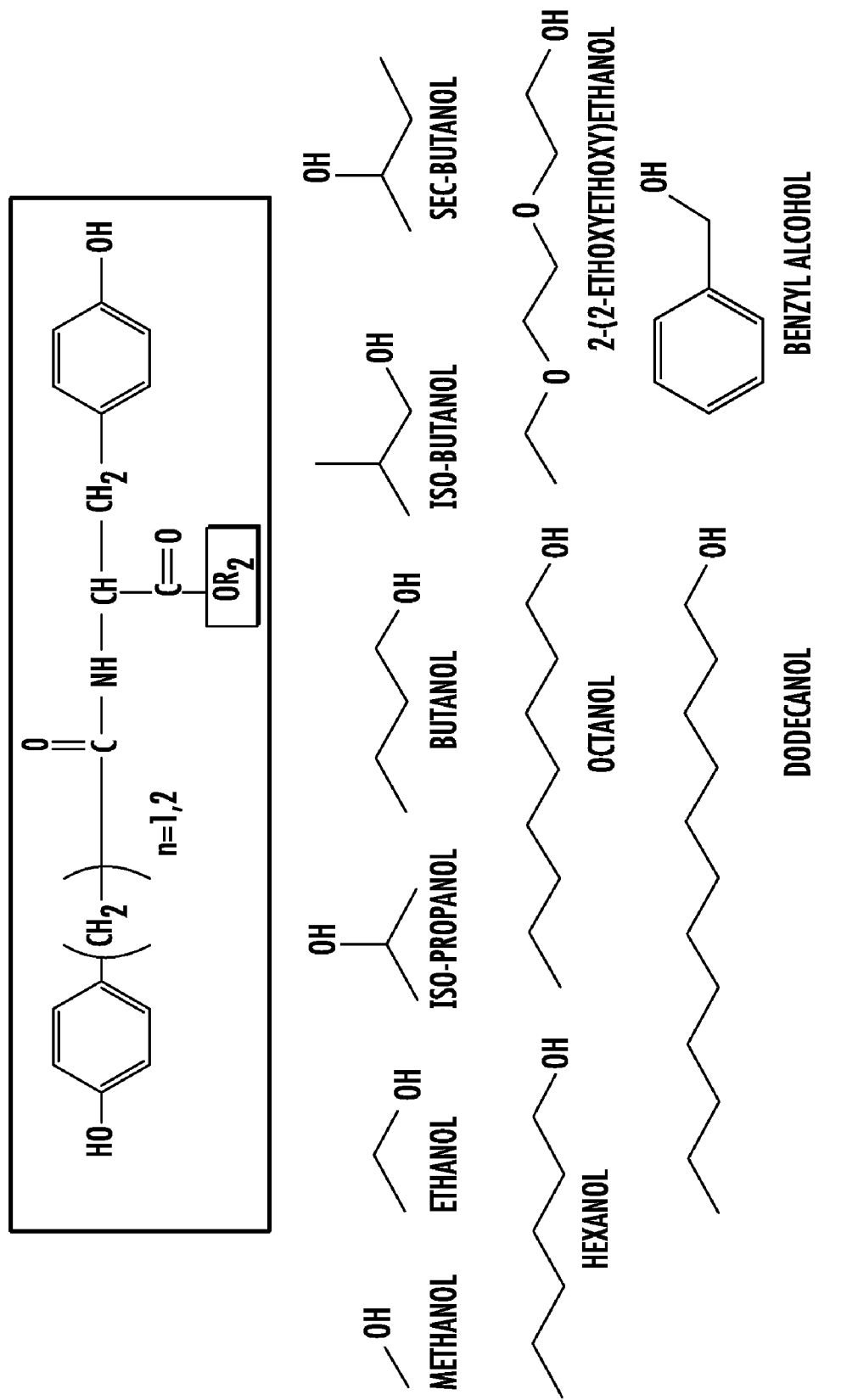

Each set of monomers was derived from a single structural template that was varied according to the schemes shown in FIG. 4. Care was taken to include only those compounds within the monomer sets of diacids and diphenols that had roughly identical reactivity at their reactive groups. In this way all polymers within the library, when prepared under identical reaction conditions, were expected to reach comparable molecular weights. Based on the above selection criteria, a total of 8 different aliphatic diacids and 14 different diphenols were identified for inclusion in the sets of monomers.

Next, a grid of small reaction vessels was set up within a water shaker bath so that each reaction vessel contained one of the 8×14=112 different monomer combinations. Although the addition of monomers and reagents was performed in a manual fashion in these initial feasibility studies, the process of dispensing the appropriate monomers and reagents within the reaction vessels could be readily automated.

Molecular weights (Mw) for the entire library of 112 polyarylates ranged from 50,000 to 150,000 g/mole. Polymer polydispersities ranged from 1.4 to 2.0. These values indicate that all polymers contained within the library were of sufficiently high molecular weight and of sufficiently similar polydispersity to allow meaningful comparisons of their respective material properties. All polymers had the expected chemical structure, as confirmed by $^1$H-NMR spectrometry.

At least one end-use property of each polymer is then measured and the variations in each measured end-use property are compared as a function of the homologous variations within the series of monomers to determine any relationship or lack thereof between the homologous variations and the series of monomers and the measured variations in end-use properties for the resulting polymers. The end-use properties may be measured simultaneously, serially or in a spatially selected manner. Measurement techniques include ELISA, SAM, chromatographic methods, DSC, TGA, DMA and TMA. Microscopic techniques may also be employed, as well as processing methods such as extrusion, solvent casting, compression molding, injection molding and microencapsulation.

End-use properties that may be measured are typically physical properties such as mechanical properties, viscoelastic properties, morphological properties, electrical properties, optical properties (such as polarizability), solute and gas permeability, thermal properties (including glass transition temperature and degradation properties), surface tension properties, and the like. Examples of morphological properties include liquid crystalline properties, phase-separated microdomain formation, the short- and long-range order of polymer chains, and the like. Examples of electrical properties include, dipole properties, pizeoelectric properties, dielectric properties, and the like.

Other end-use properties that may be measured include, but are not limited to, antibacterial activity, blood compatibility, tissue compatibility, drug release characteristics, biological interactions with living organisms, specifically the ability to support cell attachment and proliferation required for the construction of scaffolds for tissue engineering, hydrolytic degradation in vivo, protein adsorption characteristics, and the like. Still more end-use properties that may be measured include, but are not limited to, processability, radiation stability, sterilizability, adhesive properties, hydrophobic characteristics (as measured by air-water contact angle and other techniques), a stability to specific reaction conditions, and the like. For purposes of the present invention, end-use properties are also defined as including the use of the inventive method to identify monomers for condensation-type polymerization reactions that are sufficiently miscible for the condensation-type reaction to occur under interfacial or suspension polymerization process conditions.

Other end-use properties relate to self-assembly, aggregation (micelle formation) and the formation of ordered networks (gels) in aqueous or organic solutions. These properties are controlled by the hydrophilic-hydrophobic balance of the monomers used in the design of the polymeric libraries and are measured by rheological studies in solutions, dynamic light scattering, or by visualization of self-assembled aggregates by microscopic techniques such as atomic force microscopy.

Important mechanical end-use properties include tensile strength, Young's modulus and yield strength. An important thermal property is glass transition temperature. Other important end-use properties are surface tension, air-water contact angle as a measure of hydrophobicity, and biological interactions with living cells.

Figure 1:
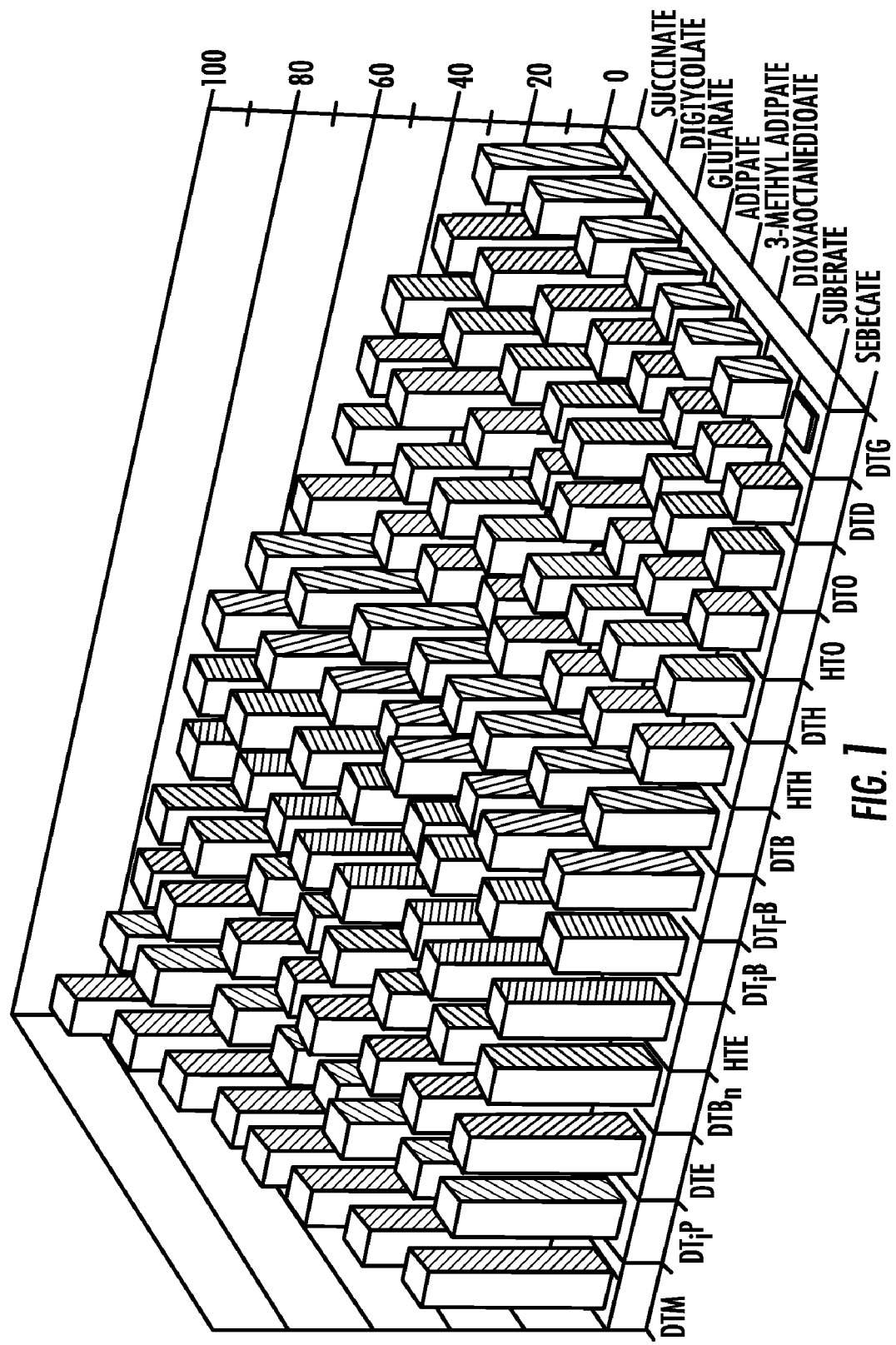
FIG. 1 depicts the correlation between polymer glass transition temperature ($T_g$) and the chemical structure of polymer backbone (y axis) and pendent chain (x axis)
Figure 2:
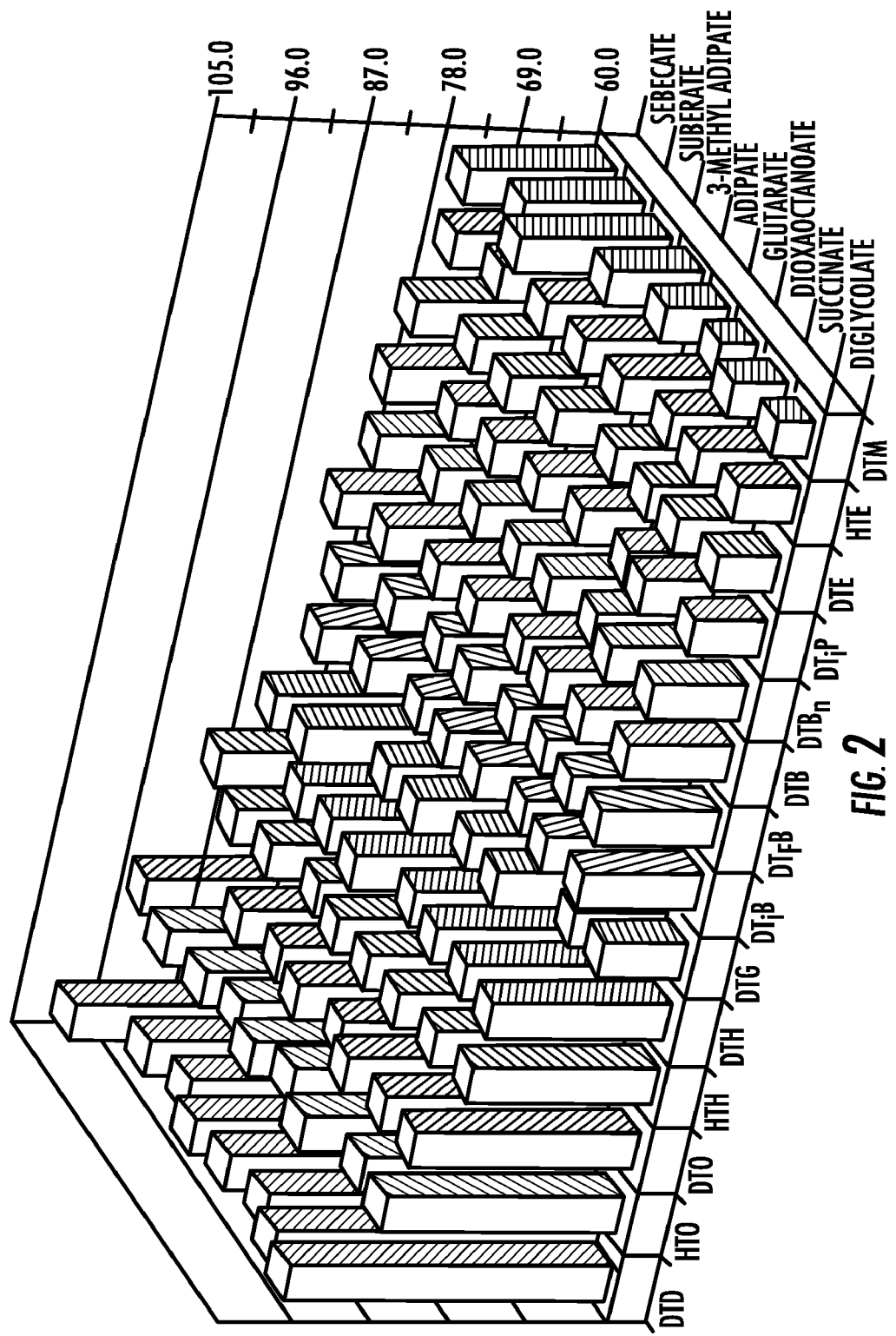
FIG. 2 depicts the correlation between the air-water contact angle (a measure of surface hydrophobicity and the chemical structure of polymer backbone (y axis) and pendent chain (x axis)

FIG. 1 depicts the glass transition temperature ($T_g$) and FIG. 2 depicts the contact angle values for each of the 112 polymers. These histograms illustrate how the values for $T_g$ and contact angle incrementally varied over a wide range. $T_g$ values ranged from 2-91° C. and increased in about 1° C. intervals from polymer to polymer while air-water contact angles ranged from 64-101° and increased in about 0.5° intervals from polymer to polymer.

There are two useful ways to create more detailed correlations that include a larger number of polymers. First, it is possible to keep the polymer backbone composition constant while varying the polymer pendent chain of the diphenol repeating unit. For example, all polymers prepared from succinic acid but carrying different pendent chain alkyl esters would be such a subgroup. Second, it is possible to look at subgroups of polymers where the pendent chain is kept constant while the polymer backbone derived from the diacid repeating unit is varied. All polymers carrying a methyl ester pendent chain but containing different diacids would be such a subgroup. Using this approach, more detailed correlations examining selected subsets of polymers within the library were developed.

FIGS. 5a and 5b depict structure-property correlations within a subset of 72 polymers whose variable regions ("Y" and "R" in FIG. 4) were aliphatic, non-oxygen containing moieties. The total flexibility index (TFI) was defined as the number of carbon atoms incorporated at the modification points in the backbone and pendent chain. The exclusion of polymers containing oxygen atoms within their variable regions made it possible to isolate the effects related to the steric bulk of the pendent chain and the mobility/flexibility of the polymer backbone.

Plots of $T_g$ and contact angle values versus TFI for these polymers are shown in FIG. 5a. These plots indicate that as TFI increases the $T_g$ values decreased in an exponential fashion and that $T_g$ values were modeled by the curve fitting equation shown in FIG. 5a. Air-water contact angles correlated with TFI in a linear fashion (FIG. 5b). Overall, varying the number of methylene groups in either the pendent chain or backbone were effective means for changing $T_g$ and contact angle over a wide range and in a predictable fashion.

Figure 6A:
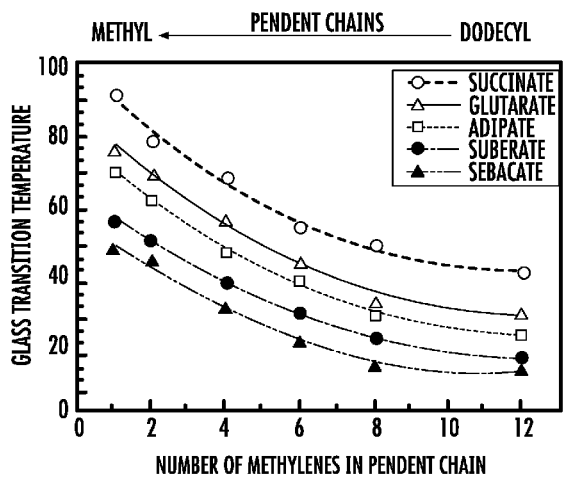
FIG. 6a depicts the correlation between $T_g$ and the number of carbon atoms incorporated at the modification point of the polymer pendent chain.
Figure 6B:
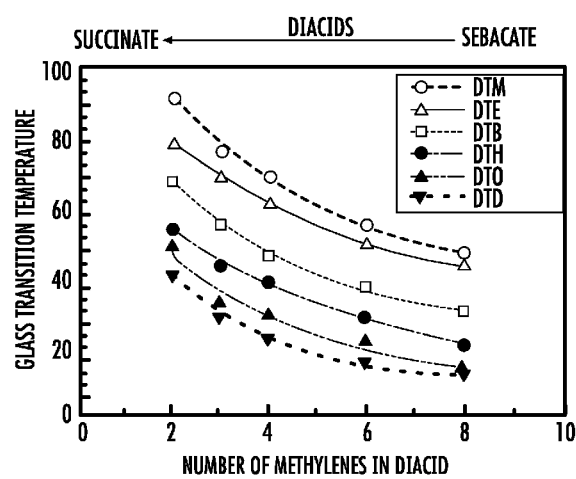
FIG. 6b depicts the correlation between $T_g$ and the number of carbon atoms incorporated at the modification point of the polymer backbone.

More specific correlations of $T_g$ and contact angle dependence on the chemical structure of the backbone and pendent chain are shown in FIGS. 6A and 6B, which are two plots illustrating how $T_g$ varies with increasing numbers of methylene groups in the pendent chain and backbone respectively. Each point in these plots represents one specific polymer (excluding polymers with branched, aromatic, and oxygen-containing variable regions "R" and "Y"). The $T_g$ values decreased exponentially as methylene groups were added to either the pendent chain or backbone. The exponential curves are non-intersecting and similar in shape indicating that alterations in either the pendent chain or backbone produced a similar change in $T_g$.

Also noteworthy of this polyarylate library is that select polymers have glass transition temperatures close to or below body temperature. Hence, devices made of these polymers can be designed to remain either in a glassy state or to assume a rubbery state when implanted.

An analogous set of plots are shown in FIGS. 7a and 7b for changes in contact angle. In contrast, there was a linear increase in the air-water contact angle as methylene groups were added to either the pendent chain or backbone. Also, unlike the $T_g$ relationships, alterations in the pendent chain or backbone produced different changes in the contact angle. The steeper curve slopes observed in the graph of contact angle vs. pendent chain suggests that surface hydrophobicity was more efficiently influenced by varying the number of methylene groups in the pendent chain The slopes were also greater for modifications on the lower methylene homologues compared to the higher homologues.

Thus, the addition of methylene groups to the pendent chain had a greater relative effect in the succinate polymers than in the sebacate polymers. It is noteworthy that such detailed and predictive correlations between polymer structure and physical properties cannot usually be obtained in the absence of the combinatorial approach described here.

Backbone branching was studied with the 3-methyl adipate series of polymers. Keeping the diphenol pendent chain constant and varying the diacid backbone was found to modestly effect $T_g$ ranging from a 2° C. increase to a 5° C. decrease with an overall average decrease of 1° C. Pendent chain branching studied with the iso- and sec-butyl esters, while keeping the diacid backbone constant, caused an average 6° C. (range 3-10° C.) increase in $T_g$ over the linear pendent chain polymers. Branching at either the pendent chain or the backbone had little discernible influence on the surface hydrophobicity as measured by the air-water contact angle.

FIGS. 1 and 2 depict that the substitution of oxygen atoms in place of methylene groups in the diphenol pendent chain and the diacid backbone had a significant effect on the glass transition temperature. Oxygen substitution in the diacid backbone increased $T_g$. Comparing the glutarate series of polymers to the diglycolate series of polymers, the replacement of one single methylene group in the diacid backbone with an oxygen atom resulted, on average, in an increase of 8° C. (range 2-13° C.) in the respective $T_g$ values.

On the other hand, oxygen substitution in the diphenol pendent chain decreased $T_g$ in a comparison of the DTG series of polymers to the comparable DTO series of polymers. The oxygen substituted DTG series had an average $T_g$ that was 13° C. (range 11-15° C.) less than the comparable fully hydrocarbon DTO series of polymers.

Oxygen substitution in either the backbone of the diacid or the pendent chain of the diphenol decreased the surface hydrophobicity of the polymers compared to the corresponding polymers having only methylene groups in their variable regions. All polymers derived from dioxaoctanedioic acid exhibited, on average, an air-water contact angle 5° (range 0-10°) less than the corresponding polymers derived from suberic acid. Similarly, all the library polymers with the oxygen-containing DTG pendent chain had air-water contact angles that were on the average 10° C. (range 2-17° C.) less than the contact angles of the corresponding DTO polymers. Still, some polymers such as poly(DTD diglycolate) (air water contact angle=97° had extremely hydrophobic surfaces in spite of the replacement of a methylene group by an oxygen atom in the polymer backbone.

The polyarylate library encompasses a broad range of mechanical properties. In qualitative terms, the stiffest of the polyarylates has mechanical properties similar to poly(D,L-lactic acid), while the most flexible polymers within the library have mechanical properties resembling those of soft polysiloxanes. The mechanical properties of a subset of eleven polymers chosen to represent a range of glass transition temperatures from 28° C. to 78° C. in approximately 5° intervals are listed in Table 1 in order of decreasing $T_g$. In this subset of materials, Young's modulus varied from 0.28-1.68 GPa and yield strength ranged from 5.8-44.8 MPa. There are no observable incremental correlations between polymer structure and stiffness or yield strength. However, those polymers whose glass transition temperature was below 35° C. showed a dramatic drop in stiffness and tensile strength that was related to their impending transition from the glassy into the rubbery state.

TABLE I

ROOM TEMPERATURE (22° C.) MECHANICAL PROPERTIES OF SELECTED POLYARYLATES

| Polymer | $T_g$ (°C.) | Young's Modulus (GPa) | Yield Stress (Mpa) | Strain at Break (%) |
|---|---|---|---|---|
| poly(DTE succinate) | 78 | 1.68 ± 0.17 | 40.7 ± 3.2 | 304 ± 102 |
| poly(DTB succinate) | 67 | 1.56 ± 0.18 | 44.8 ± 3.8 | 566 ± 36 |
| poly(DTE adipate) | 61 | 1.56 ± 0.10 | 42.0 ± 4.4 | 638 ± 152 |
| poly(DTH succinate) | 53 | 1.61 ± 0.10 | 44.8 ± 2.3 | 456 ± 103 |
| poly(DTE suberate) | 50 | 1.39 ± 0.10 | 39.9 ± 3.7 | 534 ± 91 |
| poly(DTO succinate) | 48 | 1.41 ± 0.18 | 41.9 ± 4.5 | 622 ± 68 |
| poly(DTB adipate) | 46 | 1.49 ± 0.22 | 40.5 ± 3.5 | 710 ± 96 |
| poly(DTE sebacate) | 44 | 1.44 ± 0.06 | 34.4 ± 3.1 | 657 ± 56 |
| poly(DTB suberate) | 37 | 1.24 ± 0.04 | 31.0 ± 0.8 | 138 ± 150 |
| poly(DTB sebacate) | 30 | 0.28 ± 0.03 | 5.8 ± 0.7 | 744 ± 50 |
| poly(DTO adipate) | 28 | 0.39 ± 0.09 | 7.6 ± 1.8 | 676 ± 86 |

One of the important aspects of this library of polymers is that some material properties remained reasonably constant throughout the entire library. For example, all 112 polymers had decomposition temperatures (measured by TGA, open pan, nitrogen atmosphere) above 300° C., all polymers were amorphous and readily soluble in common organic solvents (methylene chloride, chloroform, tetrahydrofuran, dimethylformamide). Thus, all polymers contained in the library could be readily processed by solvent casting, compression molding, and extrusion.

An unexpectedly systematic correlation between polymer structure and cellular response is a unique aspect of the library of polyarylates and was observed in vitro in a study of the proliferation of fibroblasts on growth surfaces prepared from a subgroup of 42 test polymers having a straight-chain diphenol pendent chain (methyl, ethyl, butyl, hexyl, octyl and dodecyl) in combination with seven straight-chain diacid backbone configurations.

Although the polymers are degradable under physiological conditions, release of leachable contaminants or degradation products is not observed and no mass loss occurs over a period of several months. Fibroblast proliferation ranged from approximating that typically seen on tissue culture polystyrene (TSPS) dishes (poly(DTM glutarate) and poly(DTM succinate)) to complete absence of any proliferation (poly (DTD adipate) and poly(DTD succinate)). In general, the proliferation of fibroblasts on materials derived from non-oxygen containing diacids exhibits a strong, linear correlation with the contact angle (FIGS. 7a and 7b). As indicated by the highly negative slopes of the curves, cell proliferation decreases as the air-water contact angle increases from 65-100°. This is in agreement with the general observation that more hydrophobic polymer surfaces are poorer cell growth substrates for fibroblasts.

Fibroblast proliferation is more sensitive to the chemical structure of the polymer than the absolute contact angle measurement. The series of polymers having a methyl ester pendent chain (DTM) are all excellent, almost equivalent growth substrates (average 91% of TCPS proliferation; range 79-115%) even though the contact angles range from 66° to 77°. Likewise, within the library there are several polymers that have comparable contact angles that support widely varying levels of cell proliferation. For example, poly(DTB sebacate) and poly(DTH adipate) have an air-water contact angle of 84°, yet cell proliferation (relative to TCPS) is 58% and 16% respectively. In other words, within each subgroup of polymers from the same diacid but having different pendent chains, cell proliferation decreases linearly as methylene groups are successively added to the pendent chain. However, this decrease is not directly correlated with the absolute contact angle measurement of the surface and the slopes of the respective regression curves are different for each of the polymer subgroups. That is, the chemical structure of the diacid in the polymer backbone modulates the cellular response to the pendent chains.

On those polymers where oxygen was substituted in the backbones (diglycolate and dioxaoctanedioates series), fibroblast proliferation was far less sensitive to pendent chain length and surface hydrophobicity. This correlation is illustrated in FIGS. 7a and 7b by the dramatically less negative slope of the linear curve fit. All polymers having oxygen-containing diacids in their backbone are unexpectedly uniformly good fibroblast growth substrates irrespective of surface hydrophobicity.

A particularly striking example of the effect of oxygen substitution on the cellular response is the direct comparison of poly(DTD glutarate) and poly(DTD diglycolate) (FIG. 7a). These two polymers have identical structures, except that one single methylene group in the backbone of poly(DTD glutarate) has been replaced by an oxygen atom in poly(DTD diglycolate). This small structural change has very little effect on the overall polymer properties and the two polymers have virtually identical air-water contact angles of 96° and 97°, respectively. Yet fibroblasts do not proliferate on poly(DTD glutarate) to any significant extent, while substantial cell proliferation is observed on identical surfaces prepared from poly(DTD diglycolate). This is a valuable finding since it demonstrates that careful polymer design makes it possible to "decouple" the correlation between surface hydrophobicity and cell proliferation.

Ertel et al., *J. Biomed. Mat. Res.*, 24 1637-1659 (1990), and Steele et al., *J. Biomater. Sci. Polymer Edn.*, 6(6), 511-532 (1994), have reported that incorporation of oxygen species into the surface by plasma glow discharge can improve cell growth. This method incorporates oxygen species in a random fashion and is associated with a corresponding reduction in the air-water contact angle. In the polyarylate library of this invention, the selective replacement of a single methylene group by a single oxygen atom occurs at a specific position in the polymer backbone and has little effect on the air-water contact angle while significantly improving the cell growth characteristics of the substrate. This finding is unprecedented in the current literature.

Therefore the present invention includes polyarylate copolymers having the structure of Formula I in which R, $R_1$, $R_2$ and b are the same as described above with respect to Formula I and at least one of R, $R_1$ and $R_2$ contain an ether linkage. $R_1$ is preferably —$CH_2$—$CH_2$— and b is preferably one. When R contains an ether linkage, $R_2$ is preferably hydrogen or an ethyl, butyl, hexyl, octyl or benzyl group.

R, when it contains an ether linkage, is preferably —$CH_2$—O—$CH_2$— or —$CH_2$—O—$CH_2$—$CH_2$—O—$CH_2$—. When $R_1$ or $R_2$ contain an ether linkage, R preferably, when aliphatic, contains from 4 to 12 carbon atoms. When aromatic, R preferably contains from 8 to 14 carbon atoms. R is even more preferably selected so that the dicarboxylic acids from which the polyarylates are polymerized are either important naturally-occurring metabolites or highly biocompatible compounds. Preferred aliphatic dicarboxylic acids therefore include the intermediate dicarboxylic acids of the cellular respiration pathway known as the Krebs Cycle. These dicarboxylic acids include alpha-ketoglutaric acid, succinic acid, fumaric acid, maleic acid and oxalacetic acid. Other preferred biocompatible materials include sebacic acid, adipic acid, oxalic acid, malonic acid, glutaric acid, pimelic acid, suberic acid and azelaic acid. Among the preferred aromatic dicarboxylic acids are terephthalic acid, isophthalic acid and bis(p-carboxyphenoxy) alkanes such bis(p-carboxyphenoxy) propane. R is most preferably selected from —$CH_2$—C (=O)—, —$CH_2$—$CH_2$—C(=O)—, —CH=CH— and (—$CH_2$—)$_z$, wherein z is an integer between two and eight, inclusive.

$R_1$ can contain an ether linkage when it is either —CHNH$L_1$ or —CHN$L_1L_2$, wherein at least one ether linkage is located in the alkyl group of $L_1$ or $L_2$. When either $R_1$ or $R_2$, contains an ether linkage the moiety is preferably —$CH_2$—$CH_2$—O—$CH_2$—$CH_2$—O—$CH_2$—$CH_2$OH. Polyarylate copolymers in accordance with the present invention have weight average molecular weights between about 20,000 and 400,000 daltons, and preferably about 100,000 daltons, measured by GPC relative to polystyrene standards without further correction.

Tyrosine-derived diphenol monomers in which either $R_1$ or $R_2$ contain at least one ether linkage are also included within the scope of the present invention. Such monomers have the structure of Formula II, in which $R_1$, $R_2$ and b are the same as described above with respect to Formula II. $R_1$ is preferably —$CH_2$—$CH_2$—, in which case $R_2$ will contain an ether linkage, preferably the aforementioned —$CH_2$—$CH_2$—O—$CH_2$—$CH_2$—O—$CH_2$—$CH_2$OH. If $R_1$ is either —CHNH$L_1$ or —CHN$L_1L_2$, wherein either $L_1$ or $L_2$ contains at least one ether linkage, then $R_2$ is preferably hydrogen or an ethyl, butyl, hexyl, octyl or benzyl group. The preferred ether linkage-containing moiety for $L_1$ or $L_2$ is also the aforementioned $CH_3$—$CH_2$—O—$CH_2$—$CH_2$—O—$CH_2$—$CH_2$OH—.

The two general features of the above-disclosed polyarylate copolymer library which dictated the choice of monomers were that specific properties including $T_g$, contact angle, mechanical properties and cellular response should vary incrementally over a wide range, and properties such as amorphous morphology, hydrolytic lability, processibility, and biocompatibility would remain broadly similar. The advantage for this juxtaposition of property variability is that structurally similar polymers can be used in applications that are related in some general ways, but disparate in others. There are significant economic incentives in this approach for developing polymers because once a material from such a library establishes itself by successfully undergoing rigorous evaluation (e.g., FDA) for an application, other library materials might then be more quickly developed for other applications. The above-described polyarylate copolymers were designed for use in medical applications requiring degradable materials. For example, a medical application might require a soft, pliable (low $T_g$) material which is hydrophobic (low contact angle), while another application might require a relatively hard, stiff (higher $T_g$) material which is hydrophilic, while both applications may require properties that are commonly shared among all library materials such as processibility by molding, biocompatibility, degradability, and amorphous morphology.

For the above-described polyarylate copolymers, the monomers were chosen to provide incremental differences in polymer free volume, bulkiness, flexibility, and hydrophobicity. Corresponding structural variations in the two sets of monomers did not affect polymers properties equally. Thus, the monomer modifications were complementary-because variation of the pendent chain did not have the same influence on polymer properties as the same modification to the polymer backbone. The three broad types of modification on the pendent chain and backbone structure were (1) simple homologative type variations to vary the number of methylene groups, (2) substitution of oxygen for methylene groups, and (3) branching. The pendent chain modifications were all carried out with the tyrosine-derived diphenols which were prepared by a common synthetic process while backbone modifications were achieved by the judicious use of commercial diacids and hydroxyphenyl alkyl acids.

Similar modifications are expected to provide useful results with the poly(amide esters) of WO 98/36013, the disclosure of which is incorporated herein by reference. The present invention therefore also includes poly(amide esters) having the structure:

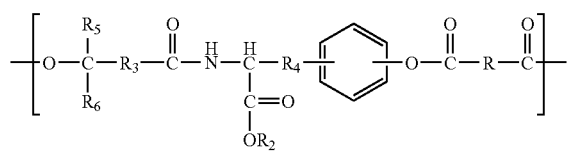

wherein $R_3$ is selected from —CH=CH—, (—CH$_2$—)$_a$, and —CHN(L$_1$L$_2$), in which a has a value from zero to two, inclusive, and L$_1$ and L$_2$ are independent-ly selected from hydrogen and straight and branched alkyl and alkylaryl groups containing up to 18 carbon atoms, provided that L$_1$ and L$_2$ are not both hydrogen. R$_5$ and R$_6$ are each independently selected from hydrogen and straight or branched alkyl groups having up to 18 carbon atoms and R$_4$ is (—CH$_2$—)$_b$, wherein b independently has a value between zero and eight, inclusive. R$_2$ is selected from straight and branched alkyl and alkylaryl groups containing up to 18 carbon atoms, and R is selected from saturated and unsaturated, substituted and unsubstituted alkyl, aryl and alkylaryl groups containing up to 18 carbon atoms. At least one of R, R$_2$, R$_5$, R$_6$ and, when R$_3$ is —CHNL$_1$L$_2$, L$_1$ or L$_2$, contains at least one ether linkage.

R$_3$ is preferably (—CH$_2$—)$_a$, with a being zero, and R$_5$ and R$_6$ are preferably independently selected from hydrogen and methyl. Most preferably, at least one of R$_5$ and R$_6$ is hydrogen, while the other, when not hydrogen is methyl. The value for b is preferably one. Thus, it is preferred that at least one of R and R$_2$ contain at least one ether linkage. Preferred ether and non-ether species for R and R$_2$ are the same as described above for the polyarylates of the present invention.

The present invention therefore also includes aliphatic-aromatic dihydroxy monomer compounds having the structure:

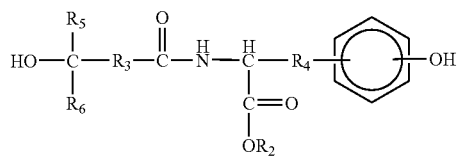

wherein $R_3$ is selected from —CH=CH—, (—CH$_2$—)$_a$, and —CHN(L$_1$L$_2$), in which a has a value from zero to two, inclusive, and L$_1$ and L$_2$ are independent-ly selected from hydrogen and straight and branched alkyl and alkylaryl groups containing up to 18 carbon atoms, provided that L$_1$ and L$_2$ are not both hydrogen, and R$_5$ and R$_6$ are each independently selected from hydrogen and straight or branched alkyl groups having up to 18 carbon atoms. R$_4$ is (—CH$_2$—)$_b$, wherein b independently has a value between zero and eight, inclusive; and R$_2$ is selected from straight and branched alkyl and alkylaryl groups containing up to 18 carbon atoms. At least one of R$_2$, R$_5$, R$_6$ and, when R$_3$ is —CHNL$_1$L$_2$, L$_1$ or L$_2$, contains at least one ether linkage. The preferred species of R$_2$, R$_3$, R$_4$, R$_5$, R$_6$, a and b are the same as described above with respect to the poly(amide esters) of the present invention. In preferred dihydroxy monomer compounds, only R$_2$ contains an ether linkage.

A basic requirement is to prepare a large enough amount of each polymer with sufficiently high molecular weight to establish basic structure-property correlations. However, because a large number of polymers are required for this methodology, there are practical requirements for practicing this methodology that the prior art does not address. First, easily purified monomers are preferred that have comparable reactivities at the polymerizable functionality so the same polymerization conditions can be used to prepare the entire library. Secondly, in order to routinely construct polymer libraries, the potential for automating the entire process is also of considerable importance. Thus, it is necessary to use mild, reproducible polymerization conditions adaptable to small scale reactions and from which the isolation and purification procedures are identical for each polymer. In order to reinforce the potential for automation, the process of isolation and purification should be designed so the individual polymers are never removed from the reaction vessel.

As noted above, the polyarylate copolymers are intended for use in medical applications. A fundamental result of the inventive methodology is that more meaningful biological correlations are derived. In vitro correlations between polymer structure and the proliferative response of rat lung fibroblasts were established. Although cell response screening studies of biomedical polymers have been conducted in the past, the lack of common structural features among test materials prevented the identification of correlations between chemical structure and cellular response. Because the polyarylate copolymers exhibited systematic variations in structure while sharing a range of common properties it was possible to correlate biological response with defined changes in the chemical structure of the tested polymers. This is a widely used approach in the pharmaceutical industry for the development of small molecule drugs, however the prior art does not address this issue with respect to the development of degradable polymeric biomaterials.

Traditionally, the biomaterial field has relied on the availability of commodity polymers rather than polymers specifically used for medical applications. This particular utility of the inventive methodology is not in the prior art associated with biomaterials development.

While specific properties that varied as a function of structural modifications have been described for the polyarylate copolymers, several properties remain essentially the same. In terms of processibility, all the polymers were soluble in common organic solvents and could be spin coated onto glass. Several test polymers were fabricated into solvent cast films, compression molded films, and extruded rods and ribbons. All 112 polymers appeared to be amorphous. The structural modifications imparted to the 112 polymers did not involve changing the hydrolytically labile moieties. While the relative hydrolytic rate of these moieties might vary, the rate differences are not expected to be great. Water uptake studies and preliminary degradation studies suggest similar amounts of water are imbibed into films fabricated from several of the library polymers with little only small differences in the rate of degradation. Finally, studies also strongly suggest that the tyrosine-derived polyarylates are biocompatible.

The inventive methodology, produced a library which facilitates the selection of polymers for biomedical applications in ways not previously possible in the prior art. For example, polymers with an air-water contact angle around 70° often lead to optimum cell attachment and proliferation. From this polymer library it is possible to choose polymers of similar structure having a 70° contact angle that span a wide $T_g$ range, including polymers that would be either glassy or rubbery at body temperature. In other subgroups of polymers, the glass transition can be kept constant while the air-water contact angle can be varied over a wide range.

The following non-limiting examples set forth hereinbelow illustrate certain aspects of the invention. All parts and percentages are by mole percent unless otherwise noted, and all temperatures are in degrees Celsius. All solvents were HPLC grade. All other reagents were of analytical grade and were used as received.

EXAMPLES

Example 1

Monomer Synthesis

Tyrosine alkyl esters were coupled with recrystallized 3-(4-hydroxyphenyl)-propionic acid (or in some cases, 4-hydroxyphenylacetic acid) using EDCI (1.0 eq.) and HOBt (0.1 eq.) in a solution of either N-methylpyrrolidinone-ethyl acetate (1:3; 1.5M concentration in tyrosine ester) or acetonitrile (0.75M concentration in tyrosine ester). After aqueous workup, the desaminotyrosyl-tyrosyl diols 1 were obtained in purities up to 99% (HPLC) and 98% (DSC). Most of the diacids 2 were commercially available in at least 99% purity. Less pure diacids 2 were recrystallized.

Example 2

Library Polymer Synthesis

Small scale polymerizations were conducted and worked up entirely in tared 20 mL glass chromatography vials with PTFE lined caps. Careful weighing of one equivalent each of the diacid 2 and desaminotyrosyl-tyrosyl diol 1 was necessary to ensure that high molecular weight material was isolated. First the diacid was weighed directly in the vial to minimize mass transfer weighing errors. Enough diacid 2 was used so one equivalent of desaminotyrosyl-tyrosyl diol 1 typically weighing in the range between 0.20-0.25 g could then be added to the vial. Dimethylaminopyridinium-p-toluenesulfonate (0.06-0.08 g), methylene chloride (4 mL), and diisopropyl-carbodiimide (0.35 mL) were then sequentially added to the vial which was tightly capped and Parafilmed. The vials were transferred to a Labline water bath shaker (model 3540) and agitated (250 rpm) at 30±1° C. for 36-48 h. Work-up consisted of diluting each vial reaction mixture with 16 mL methanol, recapping the vial, and vigorously shaking to precipitate the polymer 3, then decanting the supernatant leaving the polymer in the vial. The polymer was then dissolved in methylene chloride (1-2 mL) followed by the addition of methanol (18 mL), vigorous shaking to re-precipitate the polymer, and decanting the supernatant. Methanol (5 mL) was added to the vial and decanted as a final rinse. The polymer 3 was dried at ambient temperature in vacuum for 1 day then in vacuum at 45° C. for one day.

Example 3

Polymer Synthesis-Laboratory Scale (5-50 g)

An equimolar amount of desaminotyrosyl-tyrosyl diol 1 and diacid 2 were dissolved in methylene chloride to a concentration of 1.4 molar (in diol) in a 1 liter single-neck round bottom flask under nitrogen atmosphere. To this solution was added dimethyl aminopyridinium-p-toluenesulfonate (0.4 eq.) followed by the syringe addition of diisopropyl carbodiimide (2.5 eq.) after which the reaction generally became clear. After about 1 hour a precipitate became evident. The reaction was stirred for 24-36 hours and then was transferred to a separatory funnel and slowly added to a stirred (mechanical stirrer) solution of methanol (at least 10 volumes) to precipitate the polymer 3. The supernatant was decanted and the polymer transferred to a separatory funnel, dissolved into methylene chloride (8-10% w/v), and precipitated into either methanol or isopropanol (10 volumes). Again the supernatant was decanted and then the polymer rinsed in methanol (or isopropanol). The polymer 3 was then dried in vacuum at ambient temperature for 2-3 days then in vacuum at 45° C. for 2 days.

Molecular Weight Determination

The gel permeation chromatographic system consisted of either a Perkin Elmer pump model 250 or a Waters pump model 510, a Waters refractive index detector model 410, and either two PL-gel GPC columns (pore size $10^5$ and $10^3$ Å) or two Waters Styragel 7.8×300 mm GPC (HR3 and HR4) columns operated in series at a flow rate of 1 mL/min in THF. Molecular weights were calculated relative to polystyrene standards without further correction using Waters Millenium Chromatography Manager software on a Digital VenturisFP model 466 personal computer. Samples (5 mg/mL) were filtered (PTFE, 0.45 mL syringe filter) prior to injection.

Molecular weights and polydispersities for the library of polyarylates are shown in Table II.

TABLE II

MOLECULAR WEIGHTS (Mw = $10^3$)
AND POLYDISPERSITIES FOR THE LIBRARY OF POLYARYLATES

| | Succinic Acid | Glutaric Acid | Diglycolic Acid | Adipic Acid | 3-Methyl-Adipic Acid | Suberic Acid | Dioxaoctane-dioic Acid | Sebacic Acid |
|---|---|---|---|---|---|---|---|---|
| DTM | 61 | 76 | 11 | 77 | 100 | 44 | 18 | 113 |
| | 1.40 | 1.84 | 1.50 | 1.53 | 1.68 | 1.69 | 1.66 | 1.45 |

TABLE II-continued

MOLECULAR WEIGHTS (Mw = $10^3$)
AND POLYDISPERSITIES FOR THE LIBRARY OF POLYARYLATES

|  | Succinic Acid | Glutaric Acid | Diglycolic Acid | Adipic Acid | 3-Methyl-Adipic Acid | Suberic Acid | Dioxaoctane-dioic Acid | Sebacic Acid |
|---|---|---|---|---|---|---|---|---|
| DTE | 79 | 49 | 20 | 129 | 84 | 237 | 22 | 57 |
|  | 1.62 | 1.68 | 1.49 | 1.36 | 1.48 | 1.50 | 1.32 | 1.89 |
| DTB | 81 | 63 | 26 | 142 | 58 | 123 | 25 | 112 |
|  | 2.23 | 1.64 | 1.54 | 1.80 | 1.61 | 1.88 | 1.50 | 1.87 |
| DTH | 79 | 67 | 26 | 61 | 61 | 161 | 38 | 82 |
|  | 1.48 | 1.59 | 1.45 | 1.46 | 1.59 | 1.39 | 1.76 | 1.43 |
| DTO | 67 | 83 | 35 | 68 | 95 | 134 | 28 | 68 |
|  | 1.62 | 2.10 | 1.80 | 1.84 | 1.76 | 1.79 | 1.89 | 1.68 |
| DTD | 112 | 113 | 35 | 137 | 164 | 117 | 61 | 189 |
|  | 1.46 | 1.49 | 1.45 | 1.44 | 1.34 | 1.48 | 2.09 | 1.45 |
| DTG | 65 | 102 | 21 | 106 | 71 | 45 | 45 | 78 |
|  | 1.80 | 1.71 | 1.50 | 1.75 | 1.60 | 1.68 | 1.96 | 1.71 |
| DTiP | 78 | 89 | 31 | 32 | 58 | 33 | 36 | 88 |
|  | 2.64 | 2.93 | 1.74 | 1.47 | 1.64 | 1.54 | 1.96 | 1.66 |
| DTiB | 81 | 99 | 20 | 135 | 72 | 203 | 57 | 44 |
|  | 1.67 | 1.56 | 1.51 | 1.62 | 1.93 | 1.49 | 1.55 | 1.48 |
| DTsB | 72 | 127 | 21 | 83 | 89 | 133 | 25 | 185 |
|  | 2.08 | 1.89 | 1.57 | 1.94 | 1.82 | 2.24 | 1.73 | 1.77 |
| DTBn | 70 | 98 | 24 | 122 | 101 | 43 | 41 | 117 |
|  | 1.45 | 1.33 | 1.64 | 1.44 | 1.42 | 1.39 | 1.42 | 1.36 |
| THE | 37 | 28 | 14 | 66 | 49 | 119 | 19 | 158 |
|  | 1.73 | 1.77 | 1.49 | 1.58 | 1.82 | 1.39 | 1.47 | 1.74 |
| HTH | 46 | 51 | 17 | 54 | 74 | 103 | 42 | 134 |
|  | 1.70 | 1.70 | 1.64 | 1.57 | 1.91 | 1.57 | 1.81 | 2.03 |
| HTO | 68 | 29 | 35 | 101 | 47 | 36 | 29 | 44 |
|  | 1.95 | 1.93 | 1.62 | 1.76 | 1.94 | 1.87 | 1.65 | 1.84 |

Thermal Analysis/Differential Scanning Calorimetry (DSC)

A thermal analyzer model DSC 910 (TA Instruments, Delaware) calibrated with indium was used to determine polymer glass transition ($T_g$) temperatures and monomer absolute purities. For $T_g$ measurement, each specimen was subjected to two consecutive DSC scans with a heating rate of 10° C. min$^{-1}$. After the first run to 50° C. above $T_g$ the specimen was quenched with liquid nitrogen to at least 50° C. below $T_g$ and the second scan was immediately obtained from which the $T_g$ was determined by the midpoint on the endothermic changes associated with the glass transition. The reproducibility of the $T_g$ measurement was within 1° C. for different specimens and polymer batches. Monomer purity was measured by heating a previously dried (50° C. in vacuum) sample (2-3 mg) at a rate of 10° C. min$^{-1}$ until the temperature was ca. 20° C. below the melting point and then the heating rate reduced to 1° C. min$^{-1}$ until the temperature reaches about 10° C. above the melting point. After this heating cycle, the purity and depression were determined.

$T_g$ values for the library of polyarylates are shown in Table III.

TABLE III $T_g$ Values For The Library Of Polyarylates

|  | Succinate (1) | Diglycolate (2) | Glutarate (3) | Adipate (4) | 3-Methyl Adipate (5) | Dioxaoctane-dioate (6) | Suberate (7) | Sebacate (8) |
|---|---|---|---|---|---|---|---|---|
| DTM (1') | 91 | 82 | 76 | 69 | 68 | 63 | 55 | 47 |
| DTiP (2') | 82 | 80 | 68 | 58 | 54 | 58 | 46 | 44 |
| DTE (3') | 78 | 79 | 69 | 61 | 63 | 53 | 50 | 44 |
| DTBn (4') | 78 | 76 | 66 | 61 | 60 | 55 | 47 | 42 |
| HTB (5') | 73 | 66 | 65 | 65 | 63 | 50 | 54 | 43 |
| DTiB (6') | 75 | 72 | 62 | 56 | 47 | 50 | 42 | 33 |
| DTsB (7') | 75 | 68 | 58 | 50 | 56 | 44 | 46 | 36 |
| DTB (8') | 67 | 64 | 55 | 46 | 45 | 45 | 37 | 30 |
| HTH (9') | 59 | 46 | 42 | 32 | 38 | 31 | 27 | 23 |
| DTH (10') | 53 | 45 | 43 | 38 | 33 | 28 | 27 | 20 |
| HTO (11') | 51 | 51 | 38 | 28 | 30 | 23 | 22 | 16 |
| DTO (12') | 48 | 40 | 32 | 28 | 30 | 16 | 21 | 13 |
| DTD (13') | 40 | 36 | 28 | 22 | 19 | 17 | 15 | 12 |
| DTG (14') | 34 | 27 | 21 | 15 | 16 | 18 | 6 | 2 |

Thermal Analysis/Thermogravimetric Analysis (TGA):

The decomposition temperature (Td) was determined by thermogravimetric analysis on a TGA 951 (TA Instruments, Delaware) and was reported at 10% decrease in weight. The heating rate was 10° C. min$^{-1}$ and the average sample size was 30 mg.

Contact Angle Measurement

Air-water contact angles were measured on a Rame-Hart goniometer model 100-00-115 using double distilled water as the probe. The water was deposited onto the polyarylate spin coated glass cover slip in a small volume from above forming a sessile drop having a diameter of approximately 2.5 mm. Results were the average of at least 5 measurements (error±1°).

Contact angle values for the library of polyarylates are shown in Table IV:

measurement. After the final sonication in methylene chloride, the cover slips were rinsed twice in ethyl acetate and then sonicated twice (5 minutes) in a 2.5% (w/v) poly(styrene-silane) copolymer-ethyl acetate solution. The cover slips were soaked in this solution a further 10 minutes, then placed flat one cover slip high in glass petri dishes, and stored in an oven at 60° C. in vacuum for 2 days. After cooling to ambient temperature, the cover slips were removed from the vacuum oven and rinsed in ethyl acetate (2×) and methanol (2×), and then ethyl acetate once more before drying on crumbled aluminum foil in air for 30 minutes. The cover slips were then stored in a glass vial until needed for spin coating. Filtered (PTFE syringe filter, 0.45 mm) 2.5% (w/v) polyarylate-methylene chloride solutions were used to spin coat each glass cover slip two times to ensure a smooth surface. The polymer solution was added to provide complete coverage of the glass

TABLE IV

CONTACT ANGLE VALUES FOR THE LIBRARY OF POLYARYLATES

|  | Sebacate (1) | Suberate (2) | 3-Methyl Adipate (3) | Adipate (4) | Glutarate (5) | Dioxaoctane-dioate (6) | Succinate (7) | Diglycolate (8) |
|---|---|---|---|---|---|---|---|---|
| DTD (1') | 101.2 | 95.5 | 94.0 | 96.7 | 95.6 | 94.4 | 96.1 | 97.5 |
| HTO (2') | 90.7 | 89.5 | 88.4 | 89.9 | 87.7 | 90.4 | 86.6 | 86.9 |
| DTO (3') | 94.6 | 88.1 | 86.3 | 87.3 | 85.7 | 88.1 | 86.8 | 86.6 |
| HTH (4') | 86.6 | 85.6 | 82.9 | 84.2 | 83.3 | 83.1 | 81.8 | 80.8 |
| DTH (5') | 90.3 | 84.4 | 83.8 | 83.7 | 79.9 | 81.0 | 81.0 | 80.5 |
| DTG (6') | 86 | 85.7 | 78.6 | 79.1 | 75.6 | 75.9 | 70.3 | 70.1 |
| DTiB (7') | 82.5 | 79.7 | 76.8 | 76.9 | 76.3 | 73.7 | 74.8 | 73.9 |
| DTsB (8') | 82.1 | 78.7 | 76.4 | 75.9 | 74.0 | 73.5 | 73.7 | 73.1 |
| DTB (9') | 83.6 | 81.3 | 78.7 | 77.6 | 74.9 | 75.2 | 74.0 | 72.5 |
| DTBn (10') | 80.7 | 77.1 | 75.3 | 74.1 | 73.8 | 71.1 | 72.6 | 71.1 |
| DTiP (11') | 81.4 | 77.0 | 75.3 | 73.5 | 71.8 | 69.6 | 70.7 | 67.9 |
| DTB (12') | 79.5 | 75.9 | 75.3 | 73.0 | 69.0 | 68.5 | 68.7 | 67.3 |
| THE (13') | 77.0 | 74.8 | 72.7 | 71.4 | 70.7 | 67.7 | 68.1 | 66.3 |
| DTM (14') | 77.3 | 74.1 | 77.5 | 70.7 | 67.2 | 64.6 | 66.4 | 64.2 |

Preparation for Contact Angle Determination Spin Coated Glass Cover Slip

Glass cover slips (18 mm diameter) were sequentially sonicated twice each in solutions of 25% NaOH (10 minutes), 25% HCl (10 minutes), and 2% Micro detergent (30 minutes). The cover slips were thoroughly rinsed after each sonication with distilled deionized water and after the final rinse sequentially sonicated twice each in absolute ethanol (5 minutes) and then methylene chloride (5 minutes). The cover slips were then stored in a solution of methylene chloride until needed for spin coating and were carefully handled either with tweezers or on the edge by hand while wearing latex disposable gloves. Each polyarylate solution was prepared by first adding about 20-30 mg of polymer to a tared glass vial and adding enough methylene chloride to give a 2.5% (w/v) solution which was then filtered (PTFE syringe filter, 0.45 mm). Cover slips were removed from the methylene chloride solution and spun dried. Polymer solution was added to provide complete coverage of the glass surface which was then spun for 20 seconds at 2000 rpm. The procedure was repeated twice more to ensure a smooth surface and then the cover slips were placed into individual disposable petri dishes and dried at ambient temperature in vacuum prior to contact angle measurement.

Spin Coated Glass Cover Slip Preparation for Cell Proliferation Assays

Glass cover slips (15 mm diameter) were cleaned in the same way as were the cover slips used for contact angle surface which was then spun for 20 seconds at 2000 rpm. The cover slips were handled either with tweezers or on the edge by hand while wearing latex disposable gloves and carefully placed into individual wells in non-tissue culture treated 24-well cell culture plates which were then stored at ambient temperature in vacuum until needed for use.

Cellular Proliferation Assay

Glass coverslips previously spin coated with each of the polymers, were placed in 24 well, non-tissue culture treated polystyrene plates. Four glass coverslips for each polymer (n=4) were used in each assay and tissue culture polystyrene served as the control material. Employing a drop culture technique, $1 \times 10^4$ cells/cm$^2$ in DMEM media supplemented with 10% heat inactivated fetal bovine serum were seeded onto each surface and incubated for one hour. Following the one hour attachment period, the wells in each plate were washed with PBS to remove non-adherent cells, replenished with media, and returned to the incubator. The number of fibroblasts present on each of the surfaces was measured at seven days with the commercially available MTS colormetric assay (Promega, Madison, Wis.).

The foregoing examples illustrate how the present invention may be employed to establish a correlation between chemical structure and $T_g$, fibroblast proliferation, and air-water contact angles.

The characterization data for desaminotyrosyl-tyrosine diols not previously reported in the literature is set forth below. All diols are variations of the general structure of FIG. 3.

L-Tyrosine-N-{3-(4-hydroxyphenyl)-1-oxopropyl}-Methyl Ester, DTM n=2, $R_2$=$CH_3$—
($C_{19}H_{21}NO_5$)
Molecular Weight, 343.39.
Melting Point (C.°) 123-124.
$^1$H-NMR (200 MHz, DMSO) δ 9.25 (s, 1H, phenol), 9.16 (s, 1H, phenol), 8.27 (d, 1H, amide), 6.96 (m, 4H, aryl), 6.67 (d, 4H, aryl), 4.40 (q, 1H, a-proton), 3.59 (s, 3H, —O—$CH_3$), 2.60-2.92 (m, 4H, —$CH_2$—), 2.33 (t, 2H, —$CH_2$—).
$^{13}$C-NMR (50 MHz, DMSO) δ 172.5, 171.9, 156.2, 155.6, 131.5, 130.2, 129.2, 127.5, 115.2, 54.1, 51.9, 37.3, 36.3, 30.4.
Anal. Calcd.: C, 66.46; H, 6.17; N, 4.08. Found: C, 66.39; H, 6.26; N, 3.97.

L-Tyrosine-N-{3-(4-hydroxyphenyl)-1-oxopropyl}-Dodecyl Ester, DTD n=2, $R_2$=$CH_3$ $(CH_2)_{11}$—
$C_{30}H_{43}NO_5$
Molecular Weight, 497.68.
Melting Point (C.°) 93-94.
$^1$H-NMR (200 MHz, DMSO) δ 9.23 (s, 1H, phenol), 9.14 (s, 1H, phenol), 8.25 (d, 1H, amide), 6.96 (m, 4H, aryl), 6.65 (d, 4H, aryl), 4.38 (q, 1H, a-proton), 3.59 (t, 2H, —O—$CH_2$—), 2.60-2.86 (m, 4H, —$CH_2$—), 2.32 (t, 2H, —$CH_2$—), 1.49 (bs, 2H, [O—$CH_2$—]$CH_2$—), 1.24 (s, 18H, —$CH_2$—), 0.86 (bs, 3H, —$CH_3$).
$^{13}$C-NMR (50 MHz, DMSO) δ 172.0, 171.8, 156.3, 155.7, 131.4, 130.2, 129.2, 127.4, 115.2, 64.2, 54.2, 37.3, 36.4, 31.6, 30.5, 29.3, 29.0, 28.9, 28.3, 25.5, 22.4, 14.2.
Anal. Calcd.: C, 72.40; H, 8.71; N, 2.82. Found: C, 71.88; H, 8.58; N, 2.71.

L-Tyrosine-N-{3-(4-hydroxyphenyl)-1-oxopropyl}-Isopropyl Ester, DTiP n=2, $R_2$=$(CH_3)_2CH$—
$C_{21}H_{25}NO_5$
Molecular Weight, 371.44.
Melting Point (C.°) 79 (DSC).
$^1$H-NMR (200 MHz, DMSO) δ 9.24 (s, 1H, phenol), 9.15 (s, 1H, phenol), 8.22 (d, 1H, amide), 6.96 (m, 4H, aryl), 6.67 (d, 4H, aryl), 4.84 (quint., 1H, [O—$(CH_3)_2$]—H), 4.33 (q, 1H, a-proton), 2.82 (t, 2H, —$CH_2$—), 2.65 (t, 2H, —$CH_2$—), 2.33 (t, 2H, —$CH_2$—), 1.16 (d, 3H, —$CH_3$), 1.06 (d, 3H, —$CH_3$).
$^{13}$C-NMR (50 MHz, DMSO) δ 171.8, 171.5, 156.2, 155.7, 131.5, 130.3, 129.2, 127.4, 115.2, 68.0, 54.3, 37.3, 36.4, 30.4, 21.8, 21.6.
Anal. Calcd.: C, 67.91; H, 6.78; N, 3.77. Found: C, 67.61; H, 7.19; N, 3.54.

L-Tyrosine-N-{3-(4-hydroxyphenyl)-1-oxopropyl}-Isobutyl Ester, DTiB n=2, $R_1$=$(CH_3)_2CH$—$CH_2$—
$C_{22}H_{25}NO_5$
Molecular Weight, 385.46.
Melting Point (C.°) 104.6 (DSC).
$^1$H-NMR (200 MHz, DMSO) δ 9.23 (s, 1H, phenol), 9.15 (s, 1H, phenol), 8.26 (d, 1H, amide), 6.98 (m, 4H, aryl), 6.65 (d, 4H, aryl), 4.38 (q, 1H, a-proton), 3.78 (d, 2H, —O—$CH_2$—), 2.60-2.87 (m, 4H, —$CH_2$—), 2.32 (t, 2H, —$CH_2$—), 1.81 (m, 1H, [(—O—$CH_2$)C($CH_3$)$_2$-]H), 1.76 (d, 6H, —$CH_3$).

$^{13}$C-NMR (50 MHz, DMSO) δ 172.1, 171.8, 156.2, 155.6, 131.5, 130.2, 129.2, 127.5, 115.3, 70.3, 54.3, 37.3, 36.4, 30.4, 27.5, 19.0.
Anal. Calcd.: C, 68.55; H, 7.06; N, 3.63. Found: C, 68.60; H, 7.21; N, 3.55.

L-Tyrosine-N-{3-(4-hydroxyphenyl)-1-oxopropyl}-sec-Butyl Ester, DTsB n=2, $R_2$=$CH_3CH_2CH(CH_3)$—
$C_{22}H_{27}NO_5$
Molecular Weight, 385.46.
Melting Point (C.°) 121 (DSC).
$^1$H-NMR (200 MHz, DMSO) δ 9.24 (s, 1H, phenol), 9.15 (s, 1H, phenol), 8.24 (d, 1H, amide), 6.98 (m, 4H, aryl), 6.67 (d, 4H, aryl), 4.70 (m, 1H, —O[(—$CH_2$)C($CH_3$—)]H), 4.35 (q, 1H, a-proton), 2.60-2.90 (m, 4H, —$CH_2$—), 2.32 (t, 2H, —$CH_2$—), 1.45 (m, 2H, —$CH_2$—), 1.08 (d 3H, —$CH_3$), 0.80 (dt, 3H, —$CH_3$).
$^{13}$C-NMR (50 MHz, DMSO) δ 171.9, 171.8, 156.2, 155.7, 131.5, 130.3, 129.3, 127.4, 115.2, 72.5, 72.3, 54.4, 54.3, 37.3, 36.4, 30.4, 28.4, 28.3, 19.4, 19.3, 9.6.
Anal. Calcd.: C, 68.55; H, 7.06; N, 3.63. Found: C, 68.35; H, 7.18; N, 3.59.

L-Tyrosine-N-{3-(4-hydroxyphenyl)-1-oxopropyl}-Benzyl Ester, DTBn n=2, $R_2$=—$CH_2C_6H_5$
$C_{25}H_{25}NO_5$
Molecular Weight, 419.49.
Melting Point (C.°) 113-115.
$^1$H-NMR (200 MHz, DMSO) δ 9.25 (s, 1H, phenol), 9.16 (s, 1H, phenol), 8.31 (d, 1H, amide), 7.30 (m, 5H, aryl), 6.97 (m, 4H, aryl), 6.65 (d, 4H, aryl), 5.07 (s, 2H, Ph-$CH_2$—), 4.44 (q, 1H, a-proton), 2.59-2.89 (m, 4H, —$CH_2$—), 2.32 (t, 2H, —$CH_2$—).
$^{13}$C-NMR (50 MHz, DMSO) δ 171.9, 156.3, 155.7, 136.1, 131.5, 130.3, 129.2, 128.6, 128.3, 128.1, 127.3, 115.3, 66.1, 54.3, 37.3, 36.3, 30.4.
Anal. Calcd.: C, 71.58; H, 6.01; N, 3.34. Found: C, 71.14; H, 6.31; N, 3.16.

L-Tyrosine-N-{2-(4-hydroxyphenyl)-1-oxoethyl}-Ethyl Ester, THE n=1, $R_2$=$CH_3CH_2$
—$C_{19}H_{21}NO_5$
Molecular Weight, 343.39.
Melting Point (C.°) 124-125.
$^1$H-NMR (200 MHz, DMSO) δ 9.25 (s, 2H, phenol), 8.37 (d, 1H, amide), 6.97 (t, 4H, aryl), 6.67 (d, 4H, aryl), 4.35 (q, 1H, a-proton), 4.05 (q, 2H, —O—$CH_2$—), 3.31 (s, 2H, Ph-$CH_2$—), 2.86 (m, 2H, —$CH_2$—), 1.12 (t, 3H, —$CH_3$).
$^{13}$C-NMR (50 MHz, DMSO) δ 171.9, 170.9, 156.3, 156.0, 130.3, 130.1, 127.4, 126.4, 115.2, 115.1, 60.7, 54.2, 41.3, 36.3, 14.2.
Anal. Calcd.: C, 66.46; H, 6.17; N, 4.08. Found: C, 66.41; H, 6.31; N, 4.03.

L-Tyrosine-N-{2-(4-hydroxyphenyl)-1-oxoethyl}-Hexyl Ester, HTH n=1, $R_2$=$CH_3(CH_2)_5$—
$C_{23}H_{29}NO_5$
Molecular Weight, 399.50.
Melting Point (C.°) 106-108.

¹H-NMR (200 MHz, CDCL3) δ 7.73 (bs, 1H, phenol), 7.59 (bs, 1H, phenol), 6.91 (d, 2H, aryl), 6.64 (d, 6H, aryl), 6.07 (d, 1H, amide), 4.78 (q, 1H, a-proton), 4.12 (t, 2H, —O—CH$_2$—), 3.46 (s, 2H, Ph-CH$_2$—), 2.93 (m, 2H, —CH$_2$—), 1.62 (m, 2H, —CH$_2$—), 1.28 (bs, 6H, —CH$_2$—), 0.87 (bs, 3H, —CH$_3$).

¹³C-NMR (50 MHz, CDCl$_3$) δ 173.2, 172.6, 156.1, 155.8, 131.2, 130.6, 126.8, 125.6, 116.6, 116.2, 66.7, 53.6, 43.0, 37.1, 31.8, 28.9, 25.9, 22.9, 14.5.

Anal. Calcd.: C, 69.15; H, 7.32; N, 3.51. Found: C, 69.13; H, 7.33; N, 3.44.

L-Tyrosine-N-(2-(4-hydroxyphenyl)-1-oxoethyl)-Octyl Ester, HTO n=1, R$_2$=CH$_3$(CH$_2$)$_7$—
C$_{25}$H$_{33}$NO$_5$
Molecular Weight, 427.55.
Melting Point (C.°) 59-61.

¹H-NMR (200 MHz, CDCL3) δ 7.60 (bs, 2H, phenol), 6.90 (d, 2H, aryl), 6.67 (d, 6H, aryl), 6.07 (d, 1H, amide), 4.79 (q, 1H, a-proton), 4.14 (t, 2 H, —O—CH$_2$—), 3.46 (s, 2H, Ph-CH$_2$—), 2.93 (m, 2H, —CH$_2$—), 1.63 (bs, 2H, —CH$_2$—), 1.26 (s, 10H, —CH$_2$—), 0.86 (bs, 3H, —CH$_3$).

¹³C-NMR (50 MHz, CDCl$_3$) δ 173.2, 172.6, 156.1, 155.8, 131.2, 130.6, 126.8, 125.7, 116.6, 116.3, 66.7, 53.6, 43.0, 37.1, 32.2, 29.6, 28.9, 26.3, 23.1, 14.6.

Anal. Calcd.: C, 70.23; H, 7.78; N, 3.28. Found: C, 69.94; H, 7.46; N, 3.16.

L-Tyrosine-N-{3-(4-hydroxyphenyl)-1-oxopropyl}-{2-(2-ethoxyethoxy)ethyl}Ester, DTG n=2, R$_2$=CH$_3$CH$_2$O—CH$_2$CH$_2$O—CH$_2$CH$_2$—
C$_{24}$H$_{31}$NO$_7$
Molecular Weight, 445.53
Melting Point (° C.), oil at ambient temperature.

¹H-NMR (200 MHz, CDCl$_3$) δ 7.62-7.50 (bs, 2H, phenol), 6.88 (d, 2H, aryl), 6.70 (q, 6H, aryl), 6.34 (d, 1H, amide), 4.78 (q, 1H, a-proton), 4.17 (bs, 2H, —O—CH$_2$—), 3.60 (bs, 6H, —CH$_2$—O—CH$_2$—O—), 3.51 (q. 2H, —O—CH$_2$-Methyl), 2.90 (m, 2H, —CH$_2$—), 2.76 (m, 2H, —CH$_2$—), 2.37 (m, 2H, —CH$_2$—), 1.16 (t, 3H, —CH$_3$)

¹³C-NMR (50 Mhz. CDCl$_3$) δ 173.5, 172.2, 155.8, 155.1, 132.1, 130.8, 129.8, 127.3, 116.0, 70.9, 70.1, 69.2, 67.3, 53.9, 38.7, 37.3, 31.1, 15.5.

Anal. Calcd.: C, 64.70; H, 7.01; N, 3.14. Found: C, 64.88; H, 6.79; N, 3.03.

L-Tyrosine-n-[3-(4-hydroxyphenyl)-1-oxopropyl]-[2-(2-ethoxyethoxy)ethyl]ester DTG C$_{24}$H$_{31}$NO$_7$
Molecular Weight, 445.53
Melting Point (C.°) Boil at ambient temperature.

¹H-NMR (200 MHz, CDCl$_3$) δ 7.62-7.50 (bs, 2H, phenol), 6.88 (d, 2H aryl, 6.70 (q, 6H, aryl), 6.34 (d, 1H, amide), 4.78 (q, 1H, α-proton), 4.17 (bs, 2H, —O—CH$_2$—), 3.60 (bs, 6H, —CH$_2$—O—CH$_2$—CH$_2$—O—), 3.51 (q, 2H, —O—CH$_2$—CH$_3$), 2.90 (m, 2H, —CH$_2$—), 2.76 (m, 2H, —CH$_2$—), 2.37 (m, 2H, —CH$_2$—), 1.16 (t, 3H, —CH$_3$).

¹³C-NMR (50 MHz, CDCl$_3$) δ 173.5, 172.2, 155.8, 155.1, 132.1, 130.8, 129.8, 127.3, 116.0, 70.9, 70.1, 69.2, 67.3, 64.9, 53.9, 38.7, 37.3, 31.1, 15.5.

¹³C-NMR (50 MHz, DMSO) δ 171.9, 156.2, 155.7, 131.5, 130.3, 129.2, 127.4, 115.2, 70.1, 69.4, 68.4, 65.8, 64.0, 54.2, 37.3, 36.3, 30.4, 15.3.

Anal. Calcd.: C, 64.707; H, 7.01; N, 3.28. Found: C, 64.88; H, 6.79; N, 3.03.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A tyrosine-derived diphenol compound having the structure:

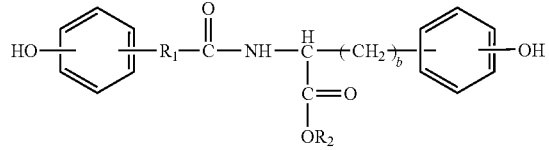

wherein R$_1$ is selected from the group consisting of —CH=CH—, (—CH$_2$—)$_a$, and

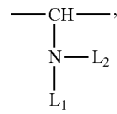

in which a has a value from zero to eight, inclusive, and L$_1$ and L$_2$ are independently selected from the group consisting of hydrogen and straight and branched alkyl and alkylaryl groups containing up to 18 carbon atoms, provided that L$_1$ and L$_2$ are not both hydrogen;

b independently has a value between zero and eight, inclusive; and

R$_2$ is selected from the group consisting of straight and branched alkyl and alkyl-aryl groups containing up to 18 carbon atoms and at least one ether linkage; and R$_1$ and (—CH$_2$—)$_b$ of said tyrosine-derived diphenol compound is ring-substituted para to phenolic oxygens.

2. The diphenol of claim 1, wherein R$_1$ is —CH$_2$—CH$_2$—, b is one and R$_2$ contains at least one ether linkage.

3. The diphenol of claim 2, wherein R$_2$ is —CH$_2$—CH$_2$—O—CH$_2$—CH$_2$—O—CH$_2$—CH$_2$—OH.

4. A condensation polymer made from the diphenol of claim 1.

5. The condensation polymer of claim 4, wherein R$_1$ of said diphenol is —CH$_2$—CH$_2$— and b is one.

6. A cell growth substrate comprising at least one polymer surface consisting essentially of the condensation polymer of claim 4.

7. The cell growth substrate according to claim 6 in the form of a solvent cast or compression molded film.

8. A drug release article comprising the condensation polymer of claim 4.

9. The article according to claim 8 in the form of a solvent cast film, a compression molded film or an extruded rod or ribbon.

* * * * *